United States Patent [19]

Hay

[11] 4,033,751

[45] July 5, 1977

[54] 2-(SUBSTITUTED-PHENYL)-HEXAHYDRO- AND TETRAHYDRO-3-(2H)-CINNOLINONES AS HERBICIDES

[75] Inventor: James Volney Hay, Newark, Del.

[73] Assignee: E. I. Du Pont de Nemours and Company, Wilmington, Del.

[22] Filed: Apr. 20, 1976

[21] Appl. No.: 678,707

[52] U.S. Cl. .................................................. 71/92
[51] Int. Cl.² .................. A01N 9/22; C07D 237/28
[58] Field of Search ..................... 71/92; 260/250 C

[56] References Cited

UNITED STATES PATENTS

| 2,797,218 | 6/1957 | Barber et al. ............... 260/250 C |
|---|---|---|
| 2,835,672 | 5/1958 | Druey et al. ................ 260/250 C |
| 3,239,524 | 3/1966 | Lowrie ............................ 71/92 X |
| 3,657,241 | 4/1972 | Kurihara ......................... 71/92 X |
| 3,749,718 | 7/1973 | Ailman ........................... 71/92 X |

OTHER PUBLICATIONS

Ried, et al., Chem. Berichte, 92, (1949), pp. 949–951.
Mondon, et al., Chem. Berichte, 96, (1963), pp. 826–839.

Primary Examiner—Joseph Paul Brust

[57] ABSTRACT

This invention relates to herbicidal 2-(substituted-phenyl)-hexahydro- and tetrahydro-3-(2H)-cinnolinones, to agricultural compositions containing such compounds, and to the method of use of these compounds as pre- and post-emergence herbicides.

21 Claims, No Drawings

2-(SUBSTITUTED-PHENYL)-HEXAHYDRO- AND TETRAHYDRO-3-(2H)-CINNOLINONES AS HERBICIDES

BACKGROUND OF THE INVENTION

Current world-wide food shortages have created a situation wherein production of crops such as soybeans, corn, wheat, etc. must be maximized. In order to maximize crop production, herbicides are needed to destroy unwanted weeds which adversely effect crop production.

In recent years, many compounds have been developed which have herbicidal activity. However, because of continuing food shortages, a need still exists for compounds which have high herbicidal activity and cause little or no damage to crops which are to be protected such as soybeans.

According to the instant invention, compounds have been discovered which have such high herbicidal activity and yet cause minimum damage to crops.

SUMMARY OF THE INVENTION

This invention relates to novel compounds of Formula I and II and their use as herbicides:

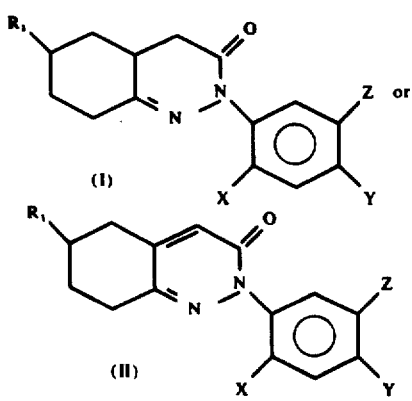

wherein:
X is chlorine, fluorine, methyl, or trifluoromethyl;
Y is chlorine, fluorine, or bromine;
Z is hydrogen, chlorine, fluorine, or $O-R_2$;
$R_1$ is hydrogen or methyl; and
$R_2$ is alkyl of 1-3 carbon atoms.

Preferred for their higher herbicidal activity are the compounds of Formula II. More preferred, for their ease of synthesis and/or higher activity are those compounds of Formula II wherein X is chlorine, fluorine or methyl and Z is hydrogen.

Most preferred for their outstanding herbicidal activity are the compounds of Formula II, where X is chlorine, fluorine or methyl, and Z and $R_1$ are both hydrogen.

Specifically preferred are:
2-(4-Chloro-2-fluorophenyl)-5,6,7,8-tetrahydrocinnolin-3(2H)-one, m.p. 104°–108° C;
2-(4-Chloro-2-methylphenyl)-5,6,7,8-tetrahydrocinnolin-3(2H)-one, m.p. 123°–126° C;
2-(4-Bromo-2-fluorophenyl)-5,6,7,8-tetrahydrocinnolin-3(2H)-one, m.p. 106°–109° C.

DETAILED DESCRIPTION OF THE INVENTION

Synthesis

The novel cinnolinones of Formula I and II are prepared as shown in Equations A and B.

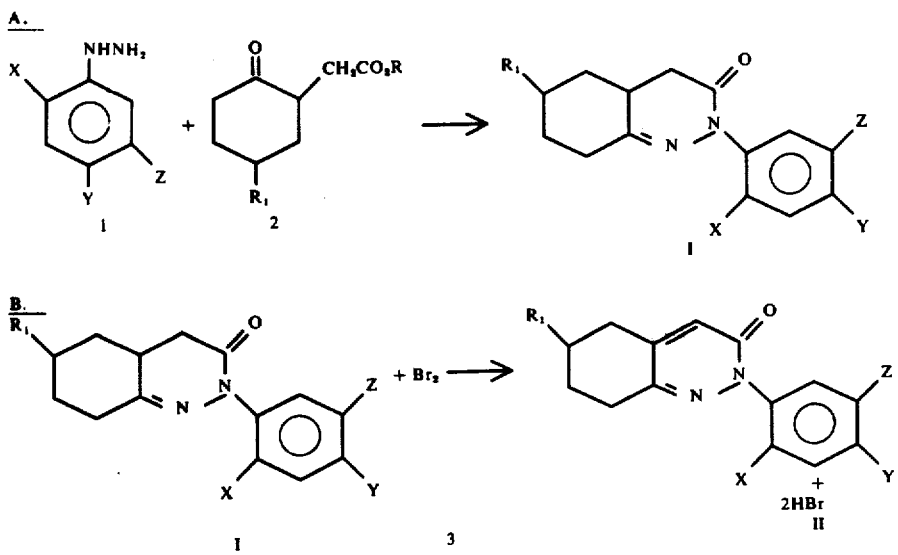

where $R_1$, X, Y, and Z are as defined above.

The preparation of hexahydro-3(2H)-cinnolinones is known in the literature. For example, the preparations of the parent hexahydrocinnolinone, unsubstituted at the 2-position, and 2-phenyl-4,4a,5,6,7,8-hexahydro-3(2H)-cinnolinone (I, $R_1 = X$, $Y$, $Z = H$) is described by R. Horning and E. Amstutz, J. Org. Chem., 20, 707 (1955), and W. Reid and A. Draisbach, Chem. Berichte, 92, 949 (1949), respectively. The preparation of tetrahydrocinnolinones of Formula II has been described. For example, the syntheses of 2-phenyl-5,6,7,8-tetrahydro-3(2H)-cinnolinone, (II, $R_1$, X, Y, Z=H) [W. Yu and H. Jing-Jain, Acta Chim. Sin., 28 (6), 351 (1962] and 2-(2,4-dinitrophenyl)-5,6,7,8-tetrahydrocinnolinone (II, $R_1$, Z=H, X, Y=NO_2$) [A. Mondon et al., Chem. Berichte, 96, 826 (1963)] have been reported, but no utility was disclosed.

The compounds of Formula I of this invention are prepared by combining the γ-ketoester 2 and the appropriate aryl hydrazine 1 in an appropriate solvent, such as lower alcohols, e.g. $C_1$–$C_3$, lower organic acids, or aromatic hydrocarbons, and optionally in the presence of an organic acid, such as acetic acid; the reaction mixture is heated at reflux for about 5–100 hours. The cinnolinone 1 is isolated by conventional techniques such as rotary evaporation of the reaction solvent. Purification of the crude product can be accomplished by recrystallization or other conventional techniques.

The novel tetrahydrocinnolinones of Formula II are prepared by the method described by R. Horning and E. Amstutz, *J. Org. Chem.*, 20, 707 (1955). Hexahydrocinnolinones of Formula I are dissolved in acetic acid, bromine is added, and the reaction mixture is heated at about 70°–120° C for 0.5–2 hours. The solvent is removed by rotary evaporation, and the crude product is partitioned between dilute aqueous base (e.g. $NaHCO_3$ or NaOH) and an inert organic solvent (e.g. $CH_2Cl_2$ or $CHCl_3$). The organic phase is dried and the solvent is removed by rotary distillation. The product obtained is the tetrahydrocinnolinone of Formula II, and may be purified by crystallization from an appropriate solvent or by other conventional techniques.

The required γ-keto esters 2 are either commercially available or are prepared by methods described in the literature: see G. Stork et al, *J. Amer. Chem. Soc.*, 76, 2029 (1954) and A. Segre et al., *J. Amer. Chem. Soc.*, 79 3503 (1957).

The preparation of hydrazines from anilines is well documented in the literature: see G. H. Coleman, *Organic Syntheses*, Coll. Vol. I, J. Wiley & Sons, New York, p. 442 and H. Kindler et al., French Pat. No. 1,419,092. The general procedure is illustrated in Equation C:

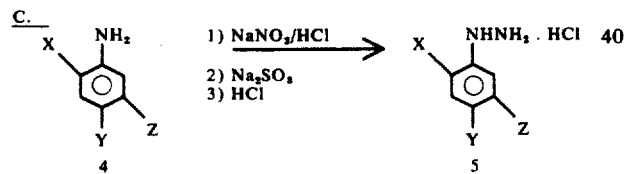

The aniline 4 is diazotized at about −10° to +5° C with sodium nitrite in aqueous acid, such as hydrochloric acid; the resulting solution is mixed with an aqueous sodium bisulfite solution at about 0°–20° C, heated to about 50°–80° C for about 0.5–2 hours and then acidified with the mineral acid to give the aryl hydrazine salt 5. The hydrazine salt often crystallizes directly from the reaction mixture and can be isolated by filtration or by other conventional techniques. In most instances, the hydrazine can be used without further purification.

Certain of the hydrazines used in preparing the compounds defined by this invention are novel; e.g. 4-chloro-2-fluorophenylhydrazine hydrochloride and 4-bromo-2-fluorophenylhydrazine hydrochloride are novel compounds which can be prepared by the method described above.

Alternatively, aryl hydrazines can be prepared from anilines by the method of M. Gibson et. al., *J. Chem. Soc.* C, 206 (1970). The general procedure is illustrated in Equation D:

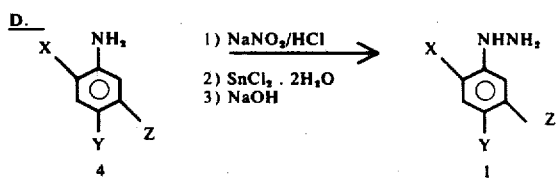

The aniline 4 is diazotized at about −10° to 5° C with sodium nitrite in concentrated hydrochloric acid; to the resulting solution is added a precooled (−40° −−50° C) solution on tin (II) dichloride dihydrate in concentrated hydrochloric acid; and the resulting reaction mixture stirred at about 0° - 25° C for 1–12 hours. A solid is formed in the reaction mixture which is collected by filtration, suspended in ice water, and made basic with an alkali metal hydroxide solution, such as 50% NaOH. The resulting aryl hydrazine can be isolated by filtration, extraction with an inert organic solvent (e.g. $CH_2Cl_2$, $CHCl_3$, or toluene), or other conventional techniques.

The aniline starting materials for these hydrazines are prepared as described below. 4-Chloro-2-fluoroaniline, for example, can be prepared from 2'-fluoroacetanilide [G. Schiemann and H. G. Baumgarten, *Chem. Berichte*, 70, 1416 (1937)] by the reaction sequence shown below:

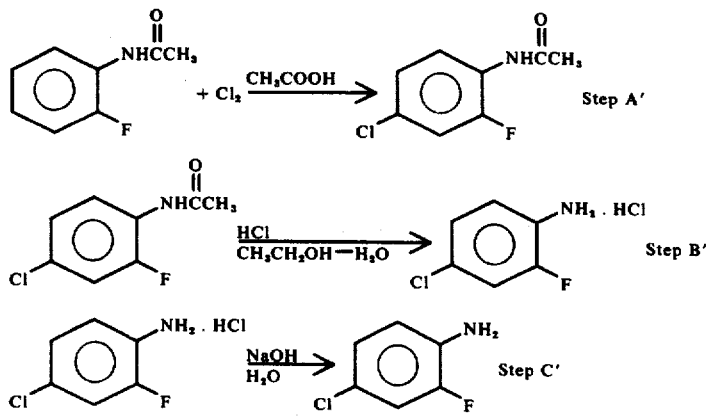

Step A'

The chlorination of acetanilides in acetic acid is well known to those skilled in the art and may be carried out under the conditions taught in W. W. Reed and K.J.P. Orton, *J. Chem. Soc.*, 91, 1543 (1907) for the chlorination of acetanilide. The chlorination of 2'-fluoroacetanilide takes place at about 25°–30° C over several hours (e.g. 5) at atmospheric pressure. The resulting product is 4'-chloro-2'-fluoroacetanilide.

STEP A'

The chlorination of acetanildies in acetic acid is well known to those skilled in the art and may be carried out under the conditions taught in W. W. Reed and K.J.P. Orton, *J. Chem. Soc.*, 91, 1543 (1907) for the chlorination or acetanilide. The chlorination of 2'-fluoroacetanilide takes placeat about 25°–30° C over several hours (e.g. 5) at atmospheric pressure. The resulting product is 4'-chloro-2'-fluoroacetanilide.

STEP B'

The chlorofluoroacetanilide is refluxed in a mixture of lower alcohol (50%) (e.g. ethanol) and concentrated hydrochloric acid (50%) for several hours (e.g. 5 or more) at about 70°–90° C and atmospheric pressure. The solvent mixture is removed at a reduced pressure of about 100–300 mm Hg and at a temperature of about 20°–50° C to leave a residue of the hydrochloride salt of 4-chloro-2-fluoroaniline.

STEP C'

After basification of an aqueous solution of the hydrochloride salt of 4-chloro-2-fluoroaniline with an alkali metal hydroxide solution, such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of about 100 to 300 mm Hg at about 20°–50° C.

4-Bromo-2-fluoroaniline can be prepared by bromination of 2-fluoroaniline [prepared in *Chem. Berichte*, 70, 416 (1937)] with N-bromosuccinimide as shown in the following equation.

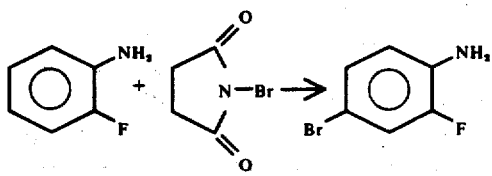

The bromination of anilines using N-bromosuccinimide in an inert organic solvent such as methylene chloride is well known to those skilled in the art, e.g., J. B. Wommack et al., *J. Het. Chem.*, 6, 243 (1969). The bromination of 2-fluoroaniline is an exothermic reaction that takes place at 0° C over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under reduced pressure of 100–300 mm Hg at 20°–50° C.

2,4-Difluoroaniline is known to the art and can be prepared by the procedure described in G. Schiemann and M. Seyhan, *Chem. Berichte*, 70, 2396 (1937).

The following examples further illustrate the method for synthesis of compounds of this invention. All parts are by weight and all temperatures in degrees centigrade unless othewise indicated.

EXAMPLE 1

Preparation of 2-(4-Chloro-2-fluorophenyl)-4,4a,5,6,7,8-hexahydro-3(2H)-cinnolinone

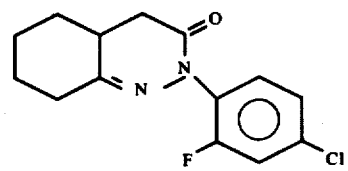

a. Preparation of 4-Chloro-2-fluoroaniline

Seventy-one parts of liquid chlorine were added to a solution of 140 parts of 2'-fluoroacetanilide in 500 parts glacial acetic acid, during 1 hour, at 25°–27°, with ice-water cooling. While stirring for 4 hours at 25°–27°, 4'-chloro-2'-fluoroacetanilide precipitated. After collecting the product by filtration, the filtrate was poured over 2000 parts ice. The resulting second portion of precipitated produce was collected by filtration, combined with the first portion and recrystallized from 700 parts of methanol at −45° to yield 119 parts of 4'-chloro-2'-fluoroacetanilide as white crystals melting at 152°–155°.

A mixture of 119 parts of 4'-chloro-2'-fluoroacetanilide in 475 parts of ethanol and 200 parts of 37% hydrochloric acid was refluxed for 17 hours and the solvent was removed under reduced pressure of 300 mm Hg to yield the moist, solid hydrochloride salt of 4-chloro-2-fluoroaniline.

The moist, solid hydrochloride salt of 4-chloro-2-fluoroaniline was cooled to 10° in ice-acetone bath and 50% aqueous sodium hydroxide was added dropwise, with stirring, until pH 11 was obtained. The resulting two-phase mixture was extracted four times; 500 parts of methylene chloride was used for each extraction. The combined organic extracts were dried with anhydrous sodium sulfate and the solvent removed under reduced pressure of 300 mm Hg to leave 89 parts of light brown, oily 4-chloro-2-fluoroaniline, $N_D^{25}$ $^t$ = 1.5541.

b. Preparation of 4-Chloro-2-fluorophenylhydrazine 20.0 parts of 4-chloro-2-fluoroaniline were dissolved in 30 parts of water and 34 parts of concentrated hydrochloric acid. The solution was cooled to 0°–10° and 32.2 parts of 30% sodium nitrite was added dropwise maintaining the temperature of the reaction between 0°–10°. After the addition was completed, the solution was stirred for 30 minutes at 0°–10°. The excess nitrite was destroyed by the addition of small amounts of sulfamic acid. When a negative test with sulfone reagent was obtained, the diazonium salt was ready for reduction. For a description see H. E. Fierz-David et al. *Fundamental Processes of Dye Chemistry* translated from 5th Austrian Ed. by P. W. Wittam, Interscience Publishers, Inc., New York, 1949, p. 243.

In a separate vessel, 35.4 parts of sodium bisulfite and 32.2 parts of 30% sodium hydroxide solution were dissolved in 140 parts of water. The solution was heated to 40°. The diazonium salt was added to the bisulfite solution over a period of about 1 hour. The mixture was heated to 70° C and 0.03 parts of sodium hydrosulfite was added. The pH was adjusted to 1.2 with 30 parts by concentrated hydrochloric acid; then an additional 90 parts of hydrochloric acid was added. The reaction mixture was heated for 1.5 hours at 70°, cooled slowly, and stirred overnight at room temperature.

Purification was achieved by heating the reaction mixture to 70° and filtering. The filtrate was cooled to 10° at which time the 4-chloro-2-fluorophenyl hydrazine hydrochloride precipitated. The product was filtered and dried to yield 10.7 parts of yellow crystalline solid, m.p. 223°.

Alternatively, 4-chloro-2-fluorophenyl hydrazine is prepared by the following method. 43.7 parts of 4-chloro-2-fluoroaniline was dissolved in 735 parts of concentrated hydrochloric acid. The solution was cooled to 0°–5° C and a solution of 22.8 parts of sodium nitrite in 187 parts water was added dropwise maintaining the temperature of the reaction between 0°–5°. The excess nitrite was destroyed by the addition of small amounts of sulfamic acid until a negative test with sulfone reagent was obtained. To the solution of the diazonium salt was added, as rapidly as possible, a solution of 170 parts stannous chloride dihydrate in 275 parts of concentrated hydrochloric acid, precooled to −50°. When the addition was complete, a heavy white precipitate formed. The reaction mixture was allowed to warm to ambient temperature over 1 hour. The precipitate was collected by filtration, then suspended in 750 parts ice-water. The pH of the solution was adjusted to 11 by the addition of 50% aqueous sodium hydroxide. The resulting aqueous suspension was extracted three times; 200 parts of methylene chloride was used for each extraction. The combined organic extracts were dried with anhydrous magnesium sulfate, and the solvent removed under reduced pressure of 300 mm Hg to leave 38.5 parts of pinkish-tan crystalline 4-chloro-2-fluorophenylhydrazine, mp 51°–63°.

c. Preparation of 2-(4-chloro-2-fluorophenyl)-4,4a,5,6,7,8-hexahydro-3(2H)-cinnolinone 8.0 Parts of 4-chloro-2-fluorophenylhydrazine and 9.2 parts of ethyl 2-cyclohexanoneacetate [bp 92°–93°, 0.5 mm Hg; prepared by the method described by A. Sergre, et al., J. Amer. Chem. Soc., 79 3503 (1957)] were dissolved in 75 parts of glacial acetic acid, and the resulting solution was refluxed for 16 hours. The reaction solvent was removed under a reduced pressure of 300 mm Hg, and the residual brown oil was dissolved in 150 parts of methylene chloride. The organic solution was washed with saturated aqueous sodium bicarbonate solution, dried with anhydrous magnesium sulfate and the solvent was removed under a reduced pressure of 300 mm Hg to give 2-(4-chloro-2-fluorophenyl)-4,4a,5,6,7,8-hexahydro-3(2H)-cinnolinone as a brown oil that solidified on scratching. Purification was achieved by recrystallization from cyclohexane to yield 5.9 parts of tan solid, mp 110°–112°.

Using the procedure of Example I with the appropriate alkyl 2-cyclohexanoneacetate and the prerequisite aryl hydrazine, the following compounds of Formula I can be prepared:

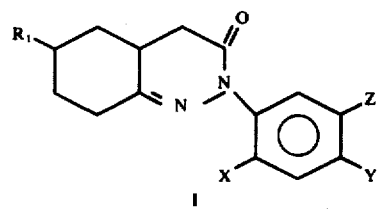

| $R_1$ | X | Y | Z | mp |
|---|---|---|---|---|
| H | F | Br | H | 99–102° |
| H | CH₃ | Cl | H | 85–88° |
| H | Cl | Cl | H | Oil |
| H | F | F | F | 79–81° |
| H | Cl | Cl | OCH₃ | |
| H | Cl | Cl | OCH(CH₃)₂ | |
| H | Cl | Cl | Cl | |
| H | CF₃ | Cl | H | |
| H | F | F | H | |
| CH₃ | F | Cl | H | 80–86° |
| CH₃ | F | Br | H | |
| CH₃ | CH₃ | Cl | H | |

EXAMPLE 2

Preparation of 2-(4-Chloro-2-fluorophenyl)-5,6,7,8-tetrahydro-3(2)-cinnolinone

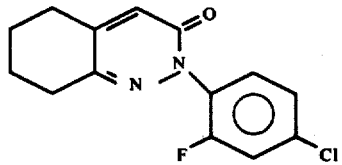

12.9 Parts of 2-(4-chloro-2-fluorophenyl)-4,4a,5,6,7,8-hexahydro-3(2H)-cinnolinone was dissolved in 30 parts of glacial acetic acid. To the reaction solution was added a solution of 7.4 parts of bromine in 5 parts glacial acetic acid. After addition was complete, the reaction solution was refluxed for 1.5 hours, then cooled, and the solvent removed under a reduced pressure of 300 mm Hg. The resulting residual brown oil was dissolved in 150 parts of methylene chloride; the organic solution was washed with saturated aqueous sodium bicarbonate solution, dried with anhydrous magnesium sulfate, and the solvent removed under a reduced pressure of 300 mm Hg. The residual brown, oily, solid was chromatographed on alumina, eluting with a mixture of ether (67% by volume) and hexane (33% by volume) to afford 2-(4-chloro-2-fluorophenyl)-5,6,7,8-tetrahydro-3(2H)-cinnolinone as a brown oil that solidified on scratching. Purification was achieved by recrystallization from benzene-hexane to yield 2.5 parts of tan crystalline solid, mp 104°–108°.

Employing the procedure of Example 2, with the appropriate 2-aryl-4,4a,5,6,7,8-hexahydro-3(2H)-cinnolinone, the following compounds of Formula II can be prepared:

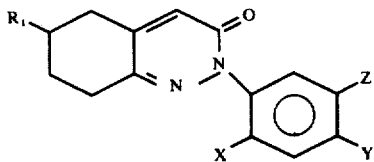

| R₁ | X | Y | Z | mp |
|---|---|---|---|---|
| H | F | Br | H | 106-109° |
| H | CH₃ | Cl | H | 123-126° |
| H | Cl | Cl | H | 96-98° |
| H | F | F | F | 146-149° |
| H | Cl | Cl | OCH₃ | |
| H | Cl | Cl | OCH(CH₃)₂ | |
| H | Cl | Cl | Cl | |
| H | CF₃ | Cl | H | |
| H | F | F | H | |
| CH₃ | F | Cl | H | 86-88° |
| CH₃ | F | Br | H | |
| CH₃ | CH₃ | Cl | H | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% surfactant(s) and (b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable aginst phase separation at 0° C. "McCutcheon's Detergents and Emulsifiers Annual", McCutcheon Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138-140, 162-164, 166, 167, 169-182.

H. Gysin and E. Knusli, U.S. Pat. No. 2,891,855, June 23, 1959, Col. 3 Line 66 through Col. 5 Line 17 and Examples 1-4.

G. C. Klingman, "Weed Control as a Science", John Wiley & Sons, Inc., New York, 1961 pp. 81-96.

J. D. Fryer and S. A. Evans, "Weed Control Handbook", 5th Edn. Blackwell Scientific Publications, Oxford, 1968, pp. 101-103.

EXAMPLE 3

| Wettable Powder | |
|---|---|
| 2-(4-chloro-2-fluorophenyl)-5,6,7,8-tetrahydrocinnolin-3-(2H)-one | 50% |
| sodium alkylnaphthalenesulfonate | 2% |
| low viscosity methyl cellulose | 2% |
| diatomaceous earth | 46% |

The ingredients are blended, coarsely hamm-milled and the air milled to produce particles of active essentially all below 10 microns in diameter. The product is reblended before packaging.

EXAMPLE 4

| Granule | |
|---|---|
| wettable powder of Example 3 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm (U.S.S. No. 18 to 40 sieves), the granules are removed, dried, and screened. Oversize material is crushed to produce additional material in the desired range. These granules contain 7.5% active ingredient.

EXAMPLE 5

| Extruded Pellet | |
|---|---|
| 2-(4-chloro-2-methylphenyl)-5,6,7,8-tetrahydrocinnolin-3(2H)-one | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

| Solution | |
|---|---|
| 2-(4-bromo-2-fluorophenyl)-5,6,7,8-tetrahydrocinnolin-3(2H)-one | 30% |
| dimethylformamide | 70% |

The ingredients are combined and stirred to produce a solution, which can be used for low volume applications.

UTILITY

The compounds of Formulae I and II are useful for the selective preemergence control of undesired vegetation in crops such as certain cereal grains, soybeans, and peanuts. These compounds are also useful for the post-emergence control of weeds in certain crops, for example, rice. Furthermore, compounds of this invention can be used as directed treatments for the pre/post-emergence control of weeds in various crops including soybeans, peanuts, cotton, and row-planted rice. In addition, these compounds are useful for broad-spectrum general weed control, such as on industrial sites, railroad and utility rights-of-way, along fences, buliding foundations, parking and storage lots, etc.

The precise amount of the compounds of Formulae I and II to be used in any given situation will vary according to the particular end result desired, the use involved, the crop weed species and soil involved, the formulation used, the mode of application, prevailing weather conditions, foliage density and the like factors. Since so many variables play a role, it is not possible to state a rate of application suitable for all situations. Broadly speaking, the compounds of the invention are used at levels of about 0.125 to 15 kilograms per hectare, preferably about 0.25 to 10 kilograms per hectare. The lower rates will generally be selected on lighter soils, soils low in organic matter content, for selective weed control in crops, or in situations where maximum persistence is not necessary.

Herbicidal activity of compounds of this invention was discovered in greenhouse tests.

PROCEDURE TEST 1

Seeds of crabgrass (Digitaria spp.), barnyardgrass (*Echinochloa crusgalli*), wild oats (*Avena fatua*), Cassia tora, morningglory (Ipomoea spp.), cocklebur (Xanthium spp.), sorghum, corn, soybean, rice, wheat and nutsedge tubers were planted in a growth medium and treated pre-emergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table I. Plant response was expressed on a scale extending from 0 = no injury to 10 = kill. Letter symbols used had the following meanings: $B$ = burn, $G$ = growth retardation, $C$ = necrosis/chlorosis, $H$ = formative effect, and $X$ = axillary stimulation.

PROCEDURE TEST II

The test was conducted in the greenhouse utilizing 10 inch diameter pots filled with Fallsington sandy loam (organic matter content approx. 1.9%).

Weed phase: Planting depth was 1 inch. One half of the pot was planted to a mixture of annual morningglory (Ipomoea spp.) and velvetleaf (*Abutilon theophrasti*), the other half to a mixture of crabgrass (Digitaria spp.), barnyardgrass (*Echinochloa crusgalli*) and giat foxtail (*Setaria faberi*).

Crop phase: Planting depth was 1 inch. Each pot contained either soybeans, corn, wheat, sugarbeets or cotton.

Within about an hour after planting, the chemicals were applied to the soil surfaces at the rates shown in the table. The solvent used was acetone.

Immediately after treatment, the pots were placed under an automatic overhead watering device where they received approximately 0.5 cm. of simulated rainfall in a period of 3 hours. On the following day the pots were transferred to the greenhouse where, from this time on, they were manually watered on a demand basis.

Plant response ratings made 29 days after treatment are shown in Table II. The ratings were made on a numerical scale extending from 0 = no injury to 10 ($\epsilon$) = complete kill. The accompanying letter symbols indicate either necrosis (C) or formative effects (H).

| Compound | Lb. Per Acre | Bush Bean | Cotton | Morning Glory | Cocklebur | Cassia | Nutsedge | POST EMERGENCE Crabgrass | Barnyard Grass | Wild Oats | Wheat | Corn | Soybean | Rice | Sorghum |
|---|---|---|---|---|---|---|---|---|---|---|---|---|---|---|---|

-continued

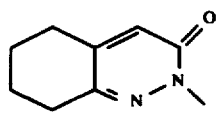

| | | | | | | | | | | | | | | |
|---|---|---|---|---|---|---|---|---|---|---|---|---|---|---|
| 2 | 9B | 9B | 10B | 9B | 5B | 8B | 10B | 10B | 9B | 9B | 8B | 9B 5X | 9B | 10B |

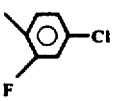

| | | | | | | | | | | | | | | |
|---|---|---|---|---|---|---|---|---|---|---|---|---|---|---|
| 2 | 9B | 8B | 9B | 7B | 5B | 7B | 10B | 10B | 9B | 9B | 8B | 9B | 9B | 9B |

| Compound | Lb. Per Acre | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
| | | | | | | PRE-EMERGENCE | | | | | | | |

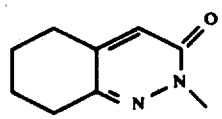

| | | | | | | | | | | | | | |
|---|---|---|---|---|---|---|---|---|---|---|---|---|---|
| 2 | 9C | 9C | 9C | 9C | 10C | 10C | 10C | 9C | 10C | 2C 7G | 9C | 10C |

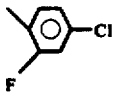

| | | | | | | | | | | | | | |
|---|---|---|---|---|---|---|---|---|---|---|---|---|---|
| 2 | 8G | 8C | 10C | 9C | 10C | 10C | 10C | 10C | 10C | 2C 7H | 9C | 10C |

TABLE II

1. - 2-(4-chloro-2-fluorophenyl)-5,6,7,8-tetrahydrocinnolin-3(2H)-one
2. - 2-(4-chloro-2-methylphenyl)-5,6,7,8-tetrahydrocinnolin-3(2H)-one
3. - 2-(4-bromo-2-fluorophenyl)-5,6,7,8-tetrahydrocinnolin-3(2H)-one

| Compound | Rate (kg/ha) | Weed Control Broadleaves[1] | Grasses[1] | Soybeans | Corn | Wheat | Sugarbeets | Cotton |
|---|---|---|---|---|---|---|---|---|
| 1 | 0.06 | 0 | 1H | | | | | |
| | 0.12 | 3C | 5H | | | | | |
| | 0.25 | 7C | 9H | 0 | 0 | 0 | 9H | 0 |
| | 0.5 | | | 0 | 0 | 0 | &H | 1H |
| | 1.0 | | | 0 | 3H | 2H | &H | 3H |
| | 1.5 | | | 0 | 5H | 5H | &H | 5H |
| | 2.0 | | | 5H | 6H | 7H | &H | 8H |
| 2 | 0.06 | 0 | 1H | | | | | |
| | 0.12 | 2C | 4H | | | | | |
| | 0.25 | 6C | 8H | 0 | 0 | 0 | 9H | 0 |
| | 0.5 | | | 0 | 0 | 1H | &H | 0 |
| | 1.0 | | | 2H | 4H | 6H | &H | 2H |
| | 1.5 | | | 5H | 5H | 7H | &H | 4H |
| | 2.0 | | | 8H | 7H | 9H | &H | 7H |
| 3 | 0.06 | 0 | 0 | | | | | |
| | 0.12 | 3C | 2H | | | | | |
| | 0.25 | 6C | 7H | 0 | 0 | 0 | &H | 0 |
| | 0.5 | | | 0 | 0 | 0 | &H | 0 |
| | 1.0 | | | 0 | 2H | 0 | &H | 0 |
| | 1.5 | | | 0 | 4H | 2H | &H | 3H |
| | 2.0 | | | 2H | 5H | 4H | &H | 6H |

TABLE II-continued

1. - 2-(4-chloro-2-fluorophenyl)-5,6,7,8-tetrahydrocinnolin-3(2H)-one
2. - 2-(4-chloro-2-methylphenyl)-5,6,7,8-tetrahydrocinnolin-3(2H)-one
3. - 2-(4-bromo-2-fluorophenyl)-5,6,7,8-tetrahydrocinnolin-3(2H)-one

| Compound | Rate (kg/ha) | Weed Control | | Crop Response | | | | |
|---|---|---|---|---|---|---|---|---|
| | | Broadleaves[1] | Grasses[2] | Soybeans | Corn | Wheat | Sugarbeets | Cotton |
| Untr. Check | — | | | | | | | |

[1] velvetleaf and morningglory
[2] Crabgrass, barnyardgrass, giant foxtail

What is claimed is:

1. A compound of the formulae:

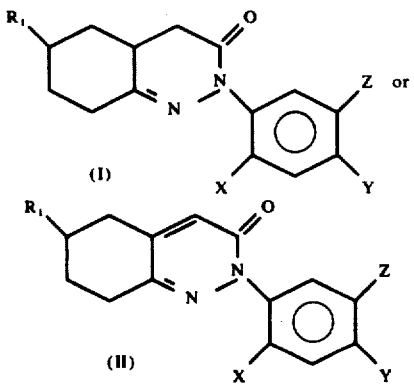

wherein:
X is chlorine, fluorine, methyl, or trifluoromethyl:
Y is chlorine, fluorine, or bromine:
Z is hydrogen, chlorine, fluorine, or O—$R_2$;
$R_1$ is hydrogen or methyl; and
$R_2$ is alkyl of 1–3 carbon atoms.

2. A compound of claim 1 which is selected from Formula II.

3. A compound of claim 1 which is selected from those compounds of Formula II where X is chlorine, fluorine or methyl and Z is hydrogen.

4. A compound of claim 1 which is selected from those compounds of Formula II where X is chlorine, fluorine or methyl and Z and $R_1$ both are hydrogen.

5. The compound of claim 1, 2-(4-chloro-2-fluorophenyl)-5,6,7,8-tetrahydrocinnolin-3(2H)-one.

6. The compound of claim 1, 2-(4-chloro-2-methylphenyl)-5,6,7,8-tetrahydrocinnolin-3(2H)-one.

7. The compound of claim 1, 2-(4-bromo-2-fluorophenyl)-5,6,7,8-tetrahydrocinnolin-3(2H)-one.

8. A composition for the control of undesirable vegetation consisting essentially of a compound of claim 1 and at least one of (a) a surface-active agent and (b) a solid or liquid diluent.

9. A composition for the control of undesirable vegetation consisting essentially of a compound of claim 2 and at least one of (a) a surface-active agent and (b) a solid or liquid diluent.

10. A composition for the control of undesirable vegetation consisting essentially of a compound of claim 3 and at least one of (a) a surface-active agent and (b) a solid or liquid diluent.

11. A composition for the control of undesirable vegetation consisting essentially of a compound of claim 4 and at least one of (a) a surface-active agent and (b) a solid or liquid diluent.

12. A composition for the control of undesirable vegetation consisting essentially of the compound of claim 5 and at least one of (a) a surface-active agent and (b) a solid or liquid diluent.

13. A composition for the control of undesirable vegetation consisting essentially of the compound of claim 6 and at least one of (a) a surface-active agent and (b) a solid or liquid diluent.

14. A composition for the control of undesirable vegetation consisting essentially of the compound of claim 7 and at least one of (a) a surface-active agent and (b) a solid or liquid diluent.

15. A method for the control of undesirable vegetation comprising applying to the locus of such undesirable vegetation a herbicidally effective amount of a compound of claim 1.

16. A method for the control of undesirable vegation comprising applying to the locus of such undesirable vegetation a herbicidally effective amount of a compound of claim 2.

17. A method for the control of undesirable vegetation comprising applying to the locus of such undesirable vegetation a herbicidally effective amount of a compound of claim 3.

18. A method for the control of undesirable vegetation comprising applying to the locus of such undesirable vegetation a herbicidally effective amount of a compound of claim 4.

19. A method for the control of undesirable vegetation comprising applying to the locus of such undesirable vegetation a herbicidally effective amount of the compound of claim 5.

20. A method for the control of undesirable vegetation comprising applying to the locus of such undesirable vegetation a herbicidally effect amount of the compound of claim 6.

21. A method for the control of undesirable vegetation comprising applying to the locus of such undesirable vegetation a herbicidally effective amount of the compound of claim 7.

* * * * *